(12) United States Patent
Sergott

(10) Patent No.: US 8,178,083 B2
(45) Date of Patent: May 15, 2012

(54) TREATMENT OF OPTIC NEURITIS

(75) Inventor: Robert Sergott, Haverford, PA (US)

(73) Assignee: Ares Trading, S.A., Aubonne (CH)

( * ) Notice: Subject to any disclaimer, the term of this patent is extended or adjusted under 35 U.S.C. 154(b) by 357 days.

(21) Appl. No.: 11/991,026

(22) PCT Filed: Aug. 30, 2006

(86) PCT No.: PCT/EP2006/065830
§ 371 (c)(1),
(2), (4) Date: Apr. 23, 2008

(87) PCT Pub. No.: WO2007/025991
PCT Pub. Date: Mar. 8, 2007

(65) Prior Publication Data
US 2008/0317711 A1 Dec. 25, 2008

Related U.S. Application Data

(60) Provisional application No. 60/713,246, filed on Sep. 1, 2005.

(51) Int. Cl.
A61K 38/21 (2006.01)
A61K 31/573 (2006.01)
A61K 38/35 (2006.01)

(52) U.S. Cl. ............... 424/85.6; 514/10.8; 514/20.8; 514/169

(58) Field of Classification Search .................. None
See application file for complete search history.

(56) References Cited

U.S. PATENT DOCUMENTS

| | | | |
|---|---|---|---|
| 4,588,585 A | 5/1986 | Mark et al. | |
| 4,737,462 A | 4/1988 | Mark et al. | |
| 4,738,931 A | 4/1988 | Sugano et al. | |
| 4,879,111 A | 11/1989 | Chong | |
| 4,904,584 A | 2/1990 | Shaw | |
| 4,959,314 A | 9/1990 | Mark et al. | |
| 4,965,195 A | 10/1990 | Namen et al. | |
| 5,017,691 A | 5/1991 | Lee et al. | |
| 5,116,943 A | 5/1992 | Koths et al. | |
| 5,155,027 A | 10/1992 | Sledzieski et al. | |
| 5,540,938 A | 7/1996 | Masterson et al. | |
| 5,541,087 A | 7/1996 | Lo et al. | |
| 5,604,229 A | 2/1997 | Fujita et al. | |
| 6,013,253 A | 1/2000 | Martin et al. | |
| 6,356,036 B1 * | 3/2002 | Zhou | 315/215 |
| 6,800,735 B2 * | 10/2004 | Whitty et al. | 530/351 |
| 7,016,048 B2 * | 3/2006 | Chen et al. | 356/497 |

FOREIGN PATENT DOCUMENTS

| | | |
|---|---|---|
| EP | 0 227 110 A2 | 12/1986 |
| EP | 0 627 406 A1 | 12/1994 |
| EP | 0 727 406 A1 | 11/1995 |
| EP | 0 778 263 A1 | 6/1997 |
| EP | 0 526 452 B1 | 2/2001 |
| JP | 2002-316985 | 10/2002 |
| WO | WO 91/08298 | 6/1991 |
| WO | WO 92/13095 | 8/1992 |
| WO | WO 96/06068 | 2/1996 |
| WO | WO 97/24137 | 7/1997 |
| WO | WO 98/48802 | 11/1998 |
| WO | WO 99/55377 | 11/1999 |
| WO | WO 99/55678 | 11/1999 |
| WO | WO 99/67230 A1 | 12/1999 |
| WO | WO 00/23472 | 4/2000 |
| WO | WO 01/03737 A1 | 1/2001 |
| WO | WO 01/45698 A1 | 6/2001 |
| WO | WO 01/47920 A1 | 7/2001 |
| WO | WO 02/18395 A1 | 3/2002 |
| WO | WO 02/28866 A2 | 4/2002 |
| WO | WO 02/076995 A2 | 10/2002 |
| WO | WO 02/080897 A1 | 10/2002 |
| WO | WO 03/020721 A1 | 3/2003 |
| WO | WO 03/068230 A1 | 8/2003 |
| WO | WO 03/070711 A1 | 8/2003 |
| WO | WO 2004/028251 A1 | 4/2004 |
| WO | WO 2004/028521 A2 * | 4/2004 |
| WO | WO 2004/043965 A1 | 5/2004 |

OTHER PUBLICATIONS

Annals of Neurology Web page retrieved from the Internet: <URL:http://www3.interscience.wiley.com/journal/110575824/abstract>. Retrieved on Feb. 19, 2010.*

Durelli L. Dose and frequency of interferon treatment matter—INCOMIN and OPTIMS. J Neurol. Dec. 2003;250 Suppl 4:IV9-IV14.*

Frohman et al. The neuro-ophthalmology of multiple sclerosis. Lancet Neurol. Feb. 2005;4(2):111-21.*

Goodin et al. Therapeutics and Technology Assessment Subcommittee of the American Academy of Neurology and the MS Council for Clinical Practice Guidelines... Neurology. Jan. 22, 2002;58(2):169-78.*

Miller JR. The importance of early diagnosis of multiple sclerosis. J Manag Care Pharm. Jun. 2004;10(3 Suppl B):S4-11.*

Pepinsky et al. Improved pharmacokinetic properties of a polyethylene glycol-modified form of interferon-beta-1a with preserved in vitro bioactivity. J Pharmacol Exp Ther. Jun. 2001;297(3):1059-66.*

(Continued)

Primary Examiner — David Romeo
(74) Attorney, Agent, or Firm — Hamilton, Brook, Smith & Reynolds, P.C.

(57) ABSTRACT

The present invention provides a method for treating a patient having demyelinating optic neuritis (DON) comprising the sequential or simultaneous administration of a steroid compound and an interferon-beta protein. It is found that early, aggressive treatment of IFN-b is beneficial in such a treatment regimen, for example where the interferon-beta protein is administered at a cumulative weekly dose of more than 12 MIL). The method according to the invention is particularly suitable and beneficial for treatment of patients having early stage DON. In particular, the DON that will benefit from being treated according to the present invention may be in subclinical stage.

31 Claims, No Drawings

OTHER PUBLICATIONS

International Preliminary Report on Patentability from counterpart International Application No. PCT/EP2006/065830, dated Apr. 2005.

Written Opinion of the International Searching Authority from counterpart International Application No. PCT/EP2006/065830, dated Mar. 24, 2008.

Balcer, Laura J., et al., "Treatment of acute demyelinating optic neuritis", *Seminars in Ophthalmology*, vol. 17, No. 1, Swets & Zeitlinger, pp. 4-10, 2002.

Beck, Roy W., "The Optic Neuritis Treatment Trial", Arch Ophthalmol, vol. 106, No. 8, pp. 1051-1053, Aug. 1988.

CHAMPS Study Group, "Interferon β-1a for Optic Neuritis Patients at High Risk for Multiple Sclerosis", *American Journal of Ophthalmology*, vol. 132, Elsevier Science Inc., pp. 463-471, 2001.

CHAMPS Study Group, "MRI predictors of early conversion to clinically definite MS in the CHAMPS placebo group", *Neurology*, vol. 59, American Academy of Neurology, pp. 998-1005, 2002.

Filippi, Massimo, "Interferon beta-1a for brain tissue loss in patients at presentation with syndromes suggestive of multiple sclerosis: a randomised, double-blind, placebo-controlled trial", The Lancet, vol. 364, pp. 1489-1496, Oct. 2004.

Foroozan, Rod, et al., "Acute demyelinating optic neuritis", Current Opinion in Ophthalmology, vol. 13, Lippincott Williams & Wilkins, Inc., pp. 375-380, 2002.

Hickman, S.J., et al., "Management of acute optic neuritis", The Lancet, vol. 360, pp. 1953-1962, Dec. 2002.

Jeffery, Douglas R., et al., "A pilot trial of combination therapy with mitoxantrone and interferon beta-1b using monthly gadolinium-enhanced magnetic resonance imaging", *Multiple Sclerosis*, vol. 11, Edward Arnold (Publishers) Ltd., pp. 296-301, 2005.

Kovacs, Birgit, et al., "Transverse myelopathy in systemic lupus erythematosus: an analysis of 14 cases and review of the literature", vol. 59, Annals of the Rheumatic Diseases, pp. 120-124, 2000.

Kume, Teruyoshi, et al., "Assessment of Coronary Intima-Media Thickness by Optical Coherence Tomography—Comparison With Intravascular Ultrasound-", vol. 69, Circulation Journal, pp. 903-907, Aug. 2005.

Manish, Nagpal, et al., "Role of Early Radial Optic Neurotomy in Central Retinal Vein Occlusion", vol. 53, No. 2, Indian Journal of Ophthalmology, pp. 115-120, 2005.

Miller, David, H., "Brain atrophy, interferon beta, and treatment trials in multiple sclerosis", The Lancet, vol. 364, pp. 1463-1464, Oct. 2004.

Myers, T.D., "Use of corticosteroid sparing systemic immunosuppression for treatment of corticosteroid dependent optic neuritis not associated with demyelinating disease", vol. 88, British J. Ophthalmol, pp. 673-680, 2004.

O'Connor, Paul, "The Effects of Intramuscular Interferon Beta-1a in Patients at High Risk for Development of Multiple Sclerosis: A Post Hoc Analysis of Data from CHAMPS", *Clinical Therapeutics*, vol. 25, No. 11, Excerpta Medica, Inc., pp. 2865-2874, 2003.

Panitch, H., et al., "Randomized, comparative study of interferon β-1a treatment regimens in MS", *Neurology*, vol. 59, Lippincott Williams & Wilkins, Inc., pp. 1496-1506, 2002.

Parisi, Vincenzo, et al., "Correlation between morphological and functional retinal impairment in multiple sclerosis patients", *IOVS*, vol. 40, No. 11, pp. 2520-2527, Oct. 1999.

PRISMS (Prevention of Relapsed and Disability by Interferon B-1a Subcutaneously in Multiple Sclerosis), Study Group, "Randomised double-blind placebo-controlled study of interferon β-1a in relapsing/remitting multiple sclerosis", The Lancet, vol. 352, pp. 1498-1504, Nov. 1998.

Pro, M.J., et al., "Retinal Nerve Fiber Layer Measurement with Optical Coherence Tomography (OCT3) in Patients with Optic Neuritis", Association for Research in Vision and Ophthalmology, Inc., 2004. Abstract.

Sandberg-Wollheim, Magnhild, "Interferon-$β_{1a}$ treatment for multiple sclerosis", *Expert Rev. Neurotherapeutics*, vol. 5, No. 1, Future Drugs Ltd., pp. 25-34, 2005.

Söderström, M., "Multiple sclerosis: rationale for early treatment", vol. 24, Neurolgy Science, pp. S298-S300, 2003.

Sorensen, P.S., et al., "Intravenous immunoglobulin G reduces MRI activity in relapsing multiple sclerosis", *Neurology*, vol. 50, American Academy of Neurology, pp. 1273-1281, 1998.

Steel, David H.W., et al., "Measurement of the retinal nerve fibre layer with scanning laser polarimetry in patients with previous demyelinating optic neuritis", vol. 64, Journal of Neurology, Neurosurgery, and Psychiatry, pp. 505-509, 1998.

Trip, S. Anand, et al., "Retinal Nerve Fiber Layer Axonal Loss and Visual Dysfunction in Optic Neuritis", *Annals of Neurology*, vol. 58, No. 3, American Neurological Association, pp. 383-391, 2005.

Wray, Shirley H., "Optic neuritis: guidelines", *Current Opinion in Neurology*, vol. 8, Current Science Ltd., pp. 72-76, 1995.

Wroe, S.J., "Effects of Dose Titration on Tolerability and Efficacy of Interferon Beta-1b in People with Multiple Sclerosis", *The Journal of Internatonal Medical Research*, vol. 33, Cambridge Medical Publications, pp. 309-318, 2005.

\* cited by examiner

TREATMENT OF OPTIC NEURITIS

RELATED APPLICATIONS

This application is the U.S. National Stage of International Application No. PCT/EP2006/065830, filed Aug. 30, 2006, published in English, and claims priority under 35 U.S.C. §119 or 365 to U.S. Application No. 60/713,246, filed Sep. 1, 2005.

FIELD OF THE INVENTION

This invention is in the field of medicine and concerns the treatment of optic neuritis. More specifically, it relates to the use of IFN-beta in treatment regimens and for the manufacture of a medicament for the treatment of patients having optic neuritis, such as for example isolated demyelinating neuritis.

BACKGROUND OF THE INVENTION

Optic neuritis is a common cause of visual loss in young adults and is also often the first manifestation of multiple sclerosis. It has been found that about 75% of patients presenting with optic neuritis progress to clinically definite multiple sclerosis (CDMS) within 15 years. The ophthalmologists may thus be the first to consider a diagnosis of multiple sclerosis.

MS is an inflammatory autoimmune disease characterized by axon demyelination and loss. A significant proportion of MS patients initially present with optic neuritis (ON), which is characterized by optic nerve damage. Clinical studies, particularly from the Optic Neuritis Study Group (ONTT), have helped clarify the natural history and treatment of optic neuritis. These studies have shown that, compared with oral prednisolone or placebo, treatment with intravenous methylprednisolone (IVMP) results in more rapid recovery of vision but without long term difference in visual acuity, see e.g., current Opin Neurol. 1995 February; 8(1):72-6 for a description of the ONTT protocol and results, reproduced herein.

The ONTT was developed to answer the following questions: (1) Does treatment of optic neuritis with either oral or intravenous steroids reduce permanent optic nerve damage? (2) Does either treatment speed recovery? (3) Are the complications of steroid treatment insignificant in relation to the magnitude of the treatment effect? To be eligible for the study, patients must have the following characteristics: acute unilateral optic neuritis with visual symptoms of eight days' duration or less; age between 18 and 45 years; no previous history of optic neuritis or optic disc pallor in the involved eye; and a relative afferent pupillary defect and a visual field defect in the involved eye. Patients entering the study will be randomized to receive one of three treatment allocations: (1) oral prednisone (1 mg/kg/d for 14 days); (2) intravenous methylprednisolone sodium succinate (1000 mg/d for three days) followed by oral prednisone for 11 days; and 3 oral placebo for 14 days. There will be short tapering off of each oral regimen. Prednisone was selected because it is the treatment currently having the most widespread use. Intravenous methylprednisolone was selected because recent experience with its use in optic neuritis and multiple sclerosis has demonstrated potentially promising results. Outcome determinations will be made during the first month to assess rate of improvement and at six months to assess the degree of residual visual dysfunction. Contrast sensitivity measured with the Pelli-Robson hart (Foresight, Syracuse, N.Y.) and perimetry performed on both the Humphrey Field Analyzer (Allergan Humphrey, San Leandro, Calif.) and Goldmann perimeter will serve as the primary determinants of treatment effect. Visual acuity and color vision will also be assessed. Contrast sensitivity was chosen as a primary measure of outcome because it is abnormal in a high percentage of cases of resolved optic neuritis and correlates well with the patient's subjective complaints.

Thus, there remains a need to improve the current protocols for the treatment of optic neuritis.

Additional clinical studies have suggested the use of interferon-beta (IFN-beta) in the context of optic neuritis or the treatment of the 1st clinical event in 'risk patients' for clinically definite multiple sclerosis:

For example, Balcer and Galetta, Semin Opthalmol. 2002 March; 17(1):4-10, suggest the treatment of demyelinating optic neuritis in patients at high risk for developing clinically definite multiple sclerosis (CDMS) with methylprednisolone i.v. (IVMP) followed by prednisone po and ifn-beta 1a at 30 microgram (mcg) i.m. 1×weekly or 22 mcg s.c. 1×weekly.

The CHAMPS study explored early use of ifn-beta at 30 mcg i.m. weekly to reduce the rate of conversion to CDMS after a 1st clinical event in 'risk patients' (MRI criteria: >2 T2-lesions) and 'high risk patients' (>9 T2-lesions, >1 gadolinium pos. lesion).

Similarly, the ETOMS study explored early use of ifn-beta at 22 mcg s.c. weekly to reduce the rate of conversion to CDMS after a 1st clinical event of risk patients (patient has >4 T2-lesions or 3 lesions one of which was infratentorial or gadolinium positive).

None of the currently available drug regimens for the treatment of optic neuritis is fully satisfactory. Accordingly, it is an object of the present invention to provide an improved treatment of optic neuritis.

SUMMARY OF THE INVENTION

The present invention provides a new and advantageous method for treating patients having ON, in particular patients having demyelinating optic neuritis (DON). The method comprises the sequential or simultaneous administration of an immunosuppressive compound, such as a steroid compound, and an interferon-beta protein. It is found that early, aggressive treatment with IFN-b is beneficial in the context of such a treatment regimen. The method according to the invention is particularly suitable and beneficial for treatment of patients having early-stage ON. In particular, early-stage ON that will benefit from being treated according to the present invention may still be in a subclinical stage when treated, i.e detectable only with the help of diagnostic tools.

DETAILED DESCRIPTION OF THE INVENTION

The present invention is based on clinical trial data showing that IFN-beta has a beneficial effect in patients with manifestations of early ON, in particular early DON. It was found that early DON is associated with structural changes related to axonal loss in the optical nerve. These structural alterations could be identified and quantified by serial optical coherence tomography (sOCT) analysis measuring the retinal nerve fiber layer (RNFL) thickness. As axon degeneration during ON and MS disease progression results in decreased RNFL density (thickness) over time, OCT can be used in ON and MS to assess the afferent visual system for axonal loss, survival, and response to treatment.

It was surprisingly found in the present invention that the observed early-stage changes in ON, such as those in the clinically unaffected eye of DON patients, can be halted, diminished and potentially reversed with early, aggressive treatment with IFN-b 1a in combination with an ON treatment according to standard treatment protocols based on immunosuppressive compounds, including steroidal drugs, such as the ONTT protocol.

Accordingly, in one aspect the present invention provides a method for treating a patient having optic neuritis (ON), comprising the sequential or simultaneous administration of a steroid compound and an interferon-beta protein wherein the interferon-beta protein is administered at a cumulative weekly dose of more than 12 MIU. Preferably, the optic neuritis treated is a demyelinating optic neuritis (DON).

In a further preferred embodiment the patient treated with a regimen according to the present invention does not have clinically definite multiple sclerosis (CDMS). The ON may, in a preferred embodiment, be an isolated manifestation (isolated optic neuritis, "clinically isolated syndrome [CIS]"). The patient presenting with ON may or may not subsequently develop CDMS.

Thus, in the context of the present invention, the ON, and in particular the DON, may be associated with any inflammatory CNS disorder, or may not be associated with a generalised inflammatory CNS disorder. The term "inflammatory CNS disorder" includes in particular demyelinating inflammatory CNS disorders, such as for example, MS, progressive multifocal leukoencephalopathy (PML), acute disseminated encephalomyelitis (ADEM) or other related diseases.

In a preferred embodiment the patient treated with a regimen according to the present invention is not at a high risk of developing clinically definite multiple sclerosis (CDMS), for example as defined according to MRI criteria. For example, in a preferred embodiment the patient treated with a regimen according to the present invention does not have 3 or more white matter lesions above 3 mm in diameter, and preferably does not have 2 or more white matter lesions above 3 mm in diameter. More preferably the patient does not have any white matter lesion above 3 mm in diameter.

In a preferred embodiment the patient treated with a regimen according to the present invention has a risk of developing clinically definite multiple sclerosis (CDMS) that is equal or below 30, 28, 26, 24 22, or even 20% at 10 years after the first diagnosis of the ON.

In a another embodiment the patient treated with a regimen according to the present invention has a low risk profile for developing clinically definite multiple sclerosis (CDMS) because the patient is male and/or presents with optic disc edema, hemorrhages or exudates when diagnosed first with ON and/or shows an absence of pain in the affected eye.

In a another embodiment the patient treated with a regimen according to the present invention may have a high risk for axonal loss and/or retinal ganglion loss when first presenting with ON. A patient having a high risk for axonal loss and/or retinal ganglion loss when first presenting with ON may for example be patient who does not improve in visual function to pulse i.v. steroid therapy within 3-4 weeks, and/or may show signs of losing axons, such as a reduction in RNFL thickness of at least 5%, 10%, 20% or even 30% in average as may be measured by OCT, such as for example serial optical coherence tomography (sOCT), or scanning laser polarimetry (SLP). Furthermore, it is understood that patients showing axonal loss of more than 5% or even more that 10% or 15% when first presenting with ON may benefit when being treated with a regimen according to the present invention. Such axonal loss may be measured by invasive or noninvasive techniques before or after initial treatment with immunosuppressive drugs, such as steroids. Preferably noninvasive in vivo biomarkers for axonal loss are measured.

The term "multiple sclerosis" within the meaning of the present invention may be defined as in the DSM-IV classification (Diagnosis and Statistical Manual of Inflammatory CNS Disorders, Fourth Edition, American Psychiatric Association, Washington D.C., 1994).

In a further preferred embodiment the DON is clinically manifest in only one optical nerve. By "clinically manifest" it is meant that a patient has at least one symptom, such as an impairment of a physiological organ function, of which he may be subjectively aware (e.g. a reduction in his clear-sightedness), or in which the physiological organ function is reduced in an amount which can be functionally ascertained. Physiological organ function that may be ascertained with regard to the optical nerve includes for example visual acuity, contrast sensitivity, color vision and the eye's visual field.

In one embodiment, the ON is not clinically manifest in the patient to be treated. Where ON is not clinically manifest, the patient will not have a reduced clear-sightedness, however, a pathological process, such as for example axon loss, may be ascertained by suitable diagnostic methods, such as for example OCT, SLP, visually evoked potentials (VEPs) or pattern electroretinogram (PERG) recordings.

In another embodiment, the patient to be treated according to the invention has a decrease in RNFL thickness of no more than 30 micron, preferably no more than 25, 20, or 15 micron in at least one eye at the onset of treatment.

In another embodiment, the patient to be treated according to the invention the patient has a decrease in RNFL thickness of at least 10 or 5 micron in at least one eye.

In one embodiment of the present invention the interferon-beta protein used is interferon-beta 1a, such as for example Avonex® or Rebif®. In another embodiment of the present invention the interferon-beta protein is interferon-beta 1b, such as for example Betaferon®.

In further embodiments of the invention the interferon-beta protein is a modified interferon-beta protein, such as a long-acting form interferon-beta. In particular, the long-acting interferon-beta may be selected from pegylated interferon-beta, interferon-beta-HAS fusion proteins, and interferon-beta-Fc-fusion proteins.

In a preferred embodiment, IFN is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

In one embodiment of the present invention the interferon-beta at is dosed at least at 44 mcg s.c. per administration. Preferably, the interferon-beta at is administered at least 3× weekly. In one particularly preferred embodiment the interferon-beta at is dosed at 44 mcg s.c. 3× weekly.

According to the invention the interferon-beta protein may be titrated to a dosage of at least 44 mcg s.c. 3× weekly within an interval of no more than 28 days, or no more than 21, or 14 or even no more than 7 days after termination of steroid treatment.

The immunosuppressive compound employed according to the present invention may for example be selected from immunosuppressants with optionally antiproliferative/antineoplastic activity, e.g. mitoxantrone, methotrexate, azathioprine, cyclophosphamide, or steroids. For example, immunosuppressants may be administered to a human in the following dosage ranges: cyclophosphamide 500-1500 mg/m2 IV; methotrexate up to 20 mg po; mitoxantrone 12 mg/m2 IV, or azathioprine 2 mg/kg p.o.

In a preferred embodiment the immunosuppressive compound is a steroid compound.

The steroid compound employed according to the present invention may be selected from the group of e.g. methylprednisolone, prednisone or dexamethasone, or steroid-secreting agents, e.g. ACTH. Steroids may be administered to a human in the following dosage ranges: methylprednisolone 1-2-mg IV, or 24-48 mg p.o.; prednisone 1 mg/kg p.o., or ACTH up to 100 MIU.

In a preferred embodiment the steroid compound is methylprednisolone.

The administration of the steroid compound and the interferon-beta protein may be sequential or simultaneous. In a preferred embodiment of the present invention the administration of the immunosuppressive compound, such as the steroid compound, and the interferon-beta protein is sequential. Preferably, the treatment with the immunosuppressive compound precedes the administration of the interferon-beta protein.

According to the present invention the steroid compound may be administered in separate dosages. In a preferred embodiment the steroid compound is administered in at least two separate dosages.

In another preferred embodiment the steroid compound is administered in accordance with the Optic Neuritis Treatment Trial (ONTT) Protocol Beck R W, Optic Neuritis Study Group. The Optic Neuritis Treatment Trial. Arch Ophthalmol 1988; 106:1051-53, reproduced herein.

Optic Neuritis Treatment Trial

The ONTT was started in 1988 when the National Eye Institute (Bethesda, Md., USA) sponsored a multicenter clinical trial of the case of corticosteroids in the treatment of acute isolated unilateral optic neuritis. The aim was to answer the following questions. Does treatment with oral prednisone or intravenous methylprednisolone improve visual outcome in acute optic neuritis? Does either treatment speed the recovery of vision? What are the complications of treatment in relation to its efficacy? By June 1991, 448 eligible patients had enrolled in a partially blinded three-armed therapeutic trial. They were randomly prescribed one of these treatments: oral prednisone (Deltasone; Upjohn, Kalamazoo, Mich., USA; 1 mg/kg body weight per day) for 14 days; intravenous methylprednisolone (Solumerdrol; Upjohn, Kalamazoo, Mich., USA; 250 mg every 6 h) for 3 days followed by oral prednisone (Deltasone, 1 mg/kg body weight per day rounded to the nearest 10 mg) for 11 days; or oral placebo for 14 days. Each treatment was followed by a short course of oral prednisone which was tapered and stopped.

Visual Outcome

Visual function was assessed after a 6- and 12-month follow-up period. The results showed that intravenous methylprednisolone followed by oral prednisone accelerated visual recovery but did not improve visual outcome and was associated with a significant increase in the rate of new attacks of optic neuritis. Within 2 years of follow-up, 30% of the prednisone-treated patients developed new bouts of optic neuritis (in either the affected or fellow eye), compared with 13% of the intravenous-treated and 16% of the placebo-treated patients. Even more important, among oral-prednisone-treated patients, the risk of a new optic neuritis attack in the fellow eye was more than double that for the placebo-treated group. Thus, by 1993, oral prednisone was considered contraindicated in the treatment of acute optic neuritis, and intravenous methylprednisolone was thought to be of marginal therapeutic value.

The treatment regimen according to the present invention may be combined with the use of additional compounds effective in MS alone or in combination. Thus, in one embodiment of the present invention a further "MS compound" (or "MS drug") is administered to the patient.

The term "interferon-beta (IFN-beta or IFN-β)", as used in the present invention, is intended to include human fibroblast interferon, which may be native, i.e. purified from a natural source, or obtained by DNA recombinant techniques from prokaryotic sources (e.g. *Escherichia coli, E. coli*) or from eukaryotic host cells, e.g. from yeast or mammalian cells. Mammalian cells such as Chinese hamster ovary cells (CHO) or human cells are a preferred host for production of recombinant IFN-beta. The IFN-beta may be glycosylated or non-glycosylated. The term "interferon-beta", as used herein, encompasses natural interferon-beta as well as interferon-beta produced by recombinant means, be it from prokaryotic (e.g. *E. coli*) or eukaryotic (e.g. CHO) hosts. If IFN-beta, used in accordance with the present invention, is non-glycosylated (e.g. produced in *E. coli*), it is preferred to administer higher amounts of IFN-beta in order to obtain a biological or pharmacological effect comparable to that of glycosylated IFN-beta. For instance, an amount of non-glycosylated IFN-beta that is about 10 times higher than the amount of glycosylated IFN-beta is preferably administered in order to obtain comparable activities. The term "interferon-beta", as used herein, also encompasses functional derivatives, muteins, analogs, and fragments, or fusion proteins of IFN-beta.

Thus, the terms "interferon (IFN)" and "interferon-beta (IFN-beta)", as used herein, are intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments.

Preferably, the IFN-beta to be used in the frame of the present invention is Avonex®, Betaseron®, or, more preferably, Rebif®.

Rebif® (interferon beta-1a) is a purified 166 amino acid glycoprotein with a molecular weight of approximately 22,500 daltons. It is produced by recombinant DNA technology using genetically engineered Chinese Hamster Ovary cells into which the human interferon beta gene has been introduced. The amino acid sequence of Rebif® is identical to that of natural fibroblast derived human interferon beta. Natural interferon beta and interferon beta-1a (Rebif®) are glycosylated with each containing a single N-linked complex carbohydrate moiety.

Using a reference standard calibrated against the World Health Organization natural interferon beta standard (Second International Standard for Interferon, Human Fibroblast GB 23 902 531), Rebif® has a specific activity of approximately 270 million international units (MIU) of antiviral activity per mg of interferon beta-1a determined in an in vitro cytopathic effect bioassay using WISH cells and Vesicular Stomatitis virus.

| Conversion table for MIU and mcg of IFN-beta | | | | |
|---|---|---|---|---|
| MIU | 3 | 12 | 18 | 24 |
| mcg | 11 | 44 | 66 | 88 |

Rebif® 44 mcg contains approximately 12 MIU of antiviral activity using this method.

Current medications for MS include disease modifying treatments, i.e. modifying the course of MS, modulate or suppress the immune system. Accordingly, MS compounds within the meaning of the present invention include the four FDA approved immunomodulating agents for RRMS: three beta interferons (Betaseron®, Berlex; Avonex®, Biogen; Rebif®, Serono) and Glatimarer Acetate (Copaxone®, Amgen). Medications for MS within the meaning of the present invention also include the FDA approved immunosuppressing drug for worsening MS, Mitoxantrone (Novantrone®, Amgen).

IFN-beta suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant human interferon-beta) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-beta in the treatment of relapsing emitting MS according to the invention depends on the type of IFN-beta used.

In accordance with the present invention, where IFN is recombinant IFN-beta 1b produced in E. Coli, commercially available under the trademark Betaseron, it may preferably be administered sub-cutaneously every second day at a dosage of about of 250 to 300 mcg or 8 MIU to 9.6 MIU per person.

In accordance with the present invention, where IFN is recombinant IFN-beta 1a, produced in Chinese Hamster Ovary cells (CHO cells), commercially available under the trademark Avonex, it may preferably be administered intramuscularly once a week at a dosage of about of 30 mcg to 33 mcg or 6 MIU to 6.6 MIU per person.

In accordance with the present invention, when IFN is recombinant IFN-beta 1a, produced in Chinese Hamster Ovary cells (CHO cells), commercially available under the trademark Rebif, it may preferably be administered sub-cutaneously three times a week (TIW) at a dosage of 22 to 44 mcg or 6 MIU to 12 MIU per person. Preferably, a dosage of 44 mcg or 12 MIU per application is chosen.

IFN-beta proteins according to the present invention may include derivatives, variants and muteins of IFN-beta.

"Functional derivatives" as used herein cover derivatives of IFN-beta, and its variants or muteins and fused proteins, which may be prepared from the functional groups which occur as side chains on the residues or the N- or C-terminal groups, by means known in the art. These functional derivatives are included in the invention as long as they remain pharmaceutically acceptable, i.e. they do not destroy the activity of the protein, which is substantially similar to, or better than, the activity of IFN-beta, and do not confer toxic properties on compositions containing it.

These derivatives may, for example, include polyethylene glycol side-chains, which may improve other properties of the protein, such as the stability, half-life, bioavailability, tolerance by the human body, or immunogenicity. To achieve this goal, IFN-beta may be linked e.g. to Polyethlyenglycol (PEG). PEGylation may be carried out by known methods, described in WO 92/13095, for example. In particular, PEG-IFN can be prepared in accordance with the teaching of WO 99/55377.

Therefore, in a preferred embodiment, the functional derivative of IFN-beta comprises at least one moiety attached to one or more functional groups, which occur as one or more side chains on the amino acid residues. An embodiment in which the moiety is a polyethylene glycol (PEG) moiety is highly preferred. In accordance with the present invention, several PEG moieties may also be attached to the IFN-beta.

Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

"Variants" or "muteins", as used in the frame of the present invention, refer to analogs of IFN-beta, in which one or more of the amino acid residues of natural IFN-beta are replaced by different amino acid residues, or are deleted, or one or more amino acid residues are added to the natural sequence IFN-beta, without diminishing considerably the activity of the resulting products as compared with the wild type IFN-beta. These muteins are prepared by known synthesis and/or by site-directed mutagenesis techniques, or any other known technique suitable therefor.

The terms "variant" or "mutein" in accordance with the present invention include proteins encoded by a nucleic acid, such as DNA or RNA, which hybridizes to DNA or RNA encoding IFN-beta as disclosed e.g. in U.S. Pat. No. 4,738,931 under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Any such variant or mutein preferably has a sequence of amino acids sufficiently duplicative of that of IFN-beta, such as to have substantially similar activity to IFN-beta. A functional assay for evaluating whether any variant or mutein has a similar activity as IFN-beta is e.g. the assay measuring the activity of interferon on the cytopathic effect of vesicular stomatitis virus in WISH cells, e.g. described by Youcefi et al., 1985. Thus, it can be determined whether any given mutein has substantially the same activity as IFN-beta by means of routine experimentation.

In a preferred embodiment, any such variant or mutein has at least 40% identity or homology with the sequence of IFN-beta as disclosed e.g. in U.S. Pat. No. 4,738,931. More preferably, it has at least 50%, at least 60%, at least 70%, at least 80% or, most preferably, at least 90% identity or homology thereto.

Muteins of IFN-beta, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IFN-beta polypeptides may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |

TABLE III-continued

Most Preferred Groups of Synonymous Amino Acids

| Amino Acid | Synonymous Group |
|---|---|
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN-beta for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

A special kind of interferon variant has been described recently. The so-called "consensus interferons" are non-naturally occurring variants of IFN (U.S. Pat. No. 6,013,253). Consensus interferons may also be used according to the invention.

"Functional derivatives" of IFN-beta as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the proteins as described above, i.e., the ability to bind the corresponding receptor and initiate receptor signaling, and do not confer toxic properties on compositions containing it. Derivatives may have chemical moieties, such as carbohydrate or phosphate residues, provided such a derivative retains the biological activity of the protein and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains, which may mask antigenic sites and extend the residence of the molecule in body fluids.

Of particular importance is a protein that has been derivatized or combined with a complexing agent to be long lasting. For example, pegylated versions, or proteins genetically engineered to exhibit long lasting activity in the body, can be used according to the present invention. A pegylated version of interferon-beta-1a has been described in WO 99/55377 and is considered as included in the definition of interferon-beta according to the present application.

In accordance with the present invention, a salt of IFN-beta may also be used for treatment of optic neuritis.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IFN-beta, which may be measured e.g. in the bioassay explained above.

The term "fused protein" refers to a polypeptide comprising IFN-beta, or a variant or mutein or fragment thereof, fused with another protein, which, e.g., has an extended residence time in body fluids. IFN-beta may thus be fused to another protein, polypeptide or the like, e.g., an immunoglobulin or a fragment thereof.

Therefore, in a further embodiment, IFN-beta comprises an immunoglobulin fusion, i.e. IFN-beta is a fused protein comprising all or part of IFN-beta fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IFN-beta. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1), or a Gly-Ser rich linker introduced between the IFN-beta sequence and the sequence derived from an immunoglobulin sequence. The resulting fusion protein has improved properties, such as an extended residence time in body fluids (half-life), increased specific activity, increased expression level, or the purification of the fusion protein is facilitated.

In a further preferred embodiment, IFN-beta is fused to the constant region of an Ig molecule, often called the Fc part of the immunoglobulin. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric. Methods of preparing immunoblobulin fusion proteins are known in the art, e.g. from EP 526 452 or from U.S. Pat. No. 5,155,027. Ig fusion proteins comprising IFN-beta moieties are described e.g. in EP 227 110, U.S. Pat. No. 5,541,087, WO 97/24137 or WO 00/23472.

A "fragment" according to the present invention refers to any subset of IFN-beta, that is, a shorter peptide, which retains the desired biological activity as measurable e.g. in the bioassay described above. Fragments may readily be prepared by removing amino acids from either end of the molecule and testing the resultant for its properties as a receptor agonist. Proteases for removing one amino acid at a time from either the N-terminal or the C-terminal of a polypeptide are known, and so determining fragments, which retain the desired biological activity, may be determined e.g. in the test described by Youcefi et al., 1985, and involves only routine experimentation.

While the present invention provides recombinant methods for making the above-defined derivatives, these derivatives may also be made by conventional protein synthesis methods, which are well known to those skilled in the art.

IFN-beta, or a variant/mutein, functional derivative, active fragment or fusion protein thereof having IFN-beta activity, is preferably administered systemically, and preferably subcutaneously or intramuscularly. Intradermal, transdermal (e.g. in slow release formulations), intravenous, oral, intracranial, epidural, topical, rectal, and intranasal routes are also within the present invention.

Any other therapeutically efficacious route of administration may also be used, for example absorption through epithelial or endothelial tissues or by gene therapy wherein a DNA molecule encoding the IFN-beta is administered to the patient (e.g. via a vector), which causes IFN-beta to be expressed and secreted in vivo.

IFN-beta may be formulated as a pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringers solution.

The term "treat" or "treating" as used herein is meant to ameliorate, alleviate symptoms, eliminate the causation of the symptoms either on a temporary or permanent basis, or to prevent or slow the appearance of symptoms of the named disorder or condition. The term "treatment" as used herein also encompasses the term "prevention of the disorder", which is, e.g., manifested by delaying the onset of the symptoms of the disorder to a medically significant extent. Treatment of the disorder is, e.g., manifested by a decrease in the symptoms associated with the disorder or an amelioration of the reoccurrence of the symptoms of the disorder.

The dosage administered, as single or multiple doses, to an individual may vary depending upon a variety of factors, including IFN-beta pharmacokinetic properties, the route of administration, patient conditions and characteristics (sex, age, body weight, health, size), extent of symptoms, concurrent treatments, frequency of treatment. Adjustment and manipulation of established dosage ranges may be determined by those skilled in the art.

Preferred doses and regimens in accordance with the present invention are selected from the group consisting of: 12 MIU (44 mcg) of IFN-beta three times a week, 12 MIU (44 mcg) daily, 24 MIU (88 mcg) three times a week, 24 MIU (88 mcg) daily. These doses are preferably administered subcutaneously.

It is also preferred to administer IFN-beta at 100 mcg (about 27 MIU) once per week intramuscularly.

The daily doses may also be given in divided doses or in sustained release form effective to obtain the desired results. Second or subsequent administrations can be performed at a dosage which is the same, less than or greater than the initial or previous dose administered to the individual.

According to a further preferred embodiment of the present invention the treatment with IFN-beta can be combined with another drug that is useful in the treatment of MS ("MS drug"). These drugs can be administered simultaneously, separately or sequentially with recombinant IFN-beta. For example, current medications for MS (MS drugs) may be modifying treatments, i.e. modifying the course of MS, modulate or suppress the immune system. Thus, MS drugs within the meaning of the present invention include Glatimarer Acetate (Copaxone®, Amgen) as well as the FDA approved immunosuppressing drug for worsening MS, Mitoxantrone (Novantrone®, Amgen). Furthermore, drugs under development for the treatment of MS may be employed according to the present invention, such as sphingosine-1-phosphate (S1 P) receptor agonists, altered peptide ligands, immunosuppressants, adenosine deaminase inhibitors, IV immunoglobulin G, monoclonal antibodies to T-cell surface markers, TH2 promoting cytokines, compounds which inhibit expression of TH1 promoting cytokines, antispasticity agents, AMPA glutamate receptor antagonists, inhibitors of VCAM-1 expression or antagonists of its ligand, anti-macrophage migration inhibitory factor, cathepsin S inhibitors and mTOR inhibitors. Thus, MS drugs within the meaning of the present invention include:

Antispasticity agents including baclofen, diazepam, piracetam and dantrolene. For example, antispasticity agents may be administered in a human in the following dosage ranges: baclofen up to 100 mg po, diazepam up to 20 mg po, piracetam up to 24 mg po, dantrolene up to 100 mg po, lamotrigine up to 100 mg/day, riluzole up to 100 mg po, tizanidine up to 12 mg po, clonidine up to 0.1 mg po, beta blockers (e.g. propanolol) up to 160 mg po, cyproheptadine up to 8 mg po, orphenadrine up to 100 mg po and cannabinoids (e.g. dronabinol) up to 5 mg po.

Adenosine deaminase inhibitors, e.g. cladribine. For example, ADA inhibitors such as cladribine may be administered to a human in a dosage range up to 0.07 mg/kg/day.

Altered peptide ligands such as glatiramer, e.g. in the acetate form. Glatiramer for example may be administered to a human in a dosage range up to 20 mg sc, or up to 50 mg po.

AMPA glutamate receptor antagonists, e.g. 2,3-dihydroxy-6-nitro-7-sulfamoylbenzo (f) quinoxaline, [1, 2, 3, 4,-tetrahydro-7-morpholin-yl-2,3-dioxo-6-(trifluoromethyl) quinoxalin-1-yl]methylphosphonate, 1-(4-aminophenyl)-4-methyl-7,8-methylene-dioxy-5H-2,3-benzodiazepine, or (−)1-(4-aminophenyl)-4-methyl-7,8-methylene-dioxy-4,5-dihydro-3-methylcarbamoyl-2,3-benzodiazepine.

Cathepsin S inhibitors. Cathepsin S inhibitors, e.g. a compound as disclosed in WO 03/20721, may for example be administered to a human in the dosage range 0.1 to 100 mg/kg/day.

Immunoglobulin G (e.g. as disclosed in Neurology, 1998, May 50 (5): 1273-81). For example, immunoglobulin G may be administered in a human in a dosage range up to 400 mg/kg IV.

Monoclonal antibodies to various T-cell surface markers, e.g. natalizumab (Antegren™, Tysabri™) or alemtuzumab. For example, monoclonal antibodies to various T-cell surface markers may be administered in a human in the following dosage ranges:natalizumab up to 3 mg/kg IV, alemtuzumab up to 30 mg sc or IV.

TH2 promoting cytokines, e.g. IL-4, IL-10, or compounds which inhibit expression of TH1 promoting cytokines, e.g. phosphodiesterase inhibitors, e.g. pentoxifylline; lamotrigine, rifluzole, tizanidine, clonidine, beta blockers, cyproheptadine, orphenadrine or cannabinoids. For example, TH2 promoting cytokines may be administered to a human in the following dosage ranges: IL-4 up to 3 llg/kg sc, or IL-10 up to 20p. g/kg sc. Compounds which inhibit expression of TH1 promoting cytokines such as the phosphodiesterase inhibitor pentoxifylline may be administered in a human in a dosage range up to 4 mg po.

Inhibitors of VCAM-1 expression or antagonists of its ligand, e.g. antagonists of thea4 I integrin VLA-4 and/or alpha-4-beta-7 integrins, e.g. natalizumab (ANTEGREN).

S1P-receptor agonists, such as S1P-receptor agonists disclosed in EP627406A1 (e.g. the compounds of formula I therein), EP0778263A1 (e.g. the compounds of formula III therein), WO02/18395 (e.g. the compounds of formula IVa or IVb therein), WO02/076995 (e.g. the compounds of formula V therein), JP2002316985 (e.g. the compounds of formula VIII therein), WO03/2914 (e.g. the compounds of formula III and IX therein). Suitable dosages and routes of administration can be readily taken from the above referenced documents for the above-mentioned compounds.

mTor inhibitors. For example, mTor inhibitors, e.g. rapamycin or a derivative thereof, e.g. 40-0-(2-hydroxyethyl)-rapamycin, may be administered in a dosage range varying from about 0.1 to 25 mg/kg/day.

Anti-Macrophage migration inhibitory factor (Anti-MIF).

Anti-inflammatory agents such as anti-inflammatory compounds described in U.S. Pat. No. 5,540,938, such as Fampridine; anti-inflammatory compounds described in WO 01/45698, such as Simvastatin; anti-inflammatory compounds described in WO 9967230, such as CDP323; anti-inflammatory compounds described in WO-2004043965, such as MLN3897; anti-inflammatory compounds described in WO 03070711; anti-inflammatory compounds described in WO 01/47920; anti-inflammatory compounds described in WO 03/068230, such as Deskar Pirfenidone; anti-inflammatory compounds described in WO 9848802, such as Xaliprodene; anti-inflammatory compounds described in WO 0228866, such as Tensirolimus; anti-inflammatory compounds described in WO 99/55678, such as Laquinimod; anti-inflammatory compounds described in EP-727,406, WO 2004/028251 and WO 2004/028251, such as Fingolimod; anti-inflammatory compounds described in WO-02080897, such as Teriflunomide.

A physician, clinician or veterinarian of ordinary skill can readily determine and prescribe the effective amount of the single active ingredients required to alleviate, counter or arrest the progress of the condition. Optimal precision in achieving concentration of the active ingredients within the range that yields efficacy without toxicity requires a regimen based on the kinetics of the active ingredients availability to target sites.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Example 1

Evaluating Effect of Subcutaneous Interferon Beta-1a on Axon Survival Using Optical Coherence Tomography in Optic Neuritis Objective: To evaluate effect of subcutaneous interferon beta-1a (Rebif) on axonal loss/survival in demyelinating optic neuritis (ON) associated with multiple sclerosis (MS) using optical coherence tomography (OCT). A case study is presented.

Methods: The patient underwent a standard neuro-ophthalmic examination, including visual acuity, afferent pupil defect, intraocular pressure, and color vision testing. MRI assessed brain and spinal cord lesion load. For purposes of analysis, each eye was divided into 12 sectors and OCT measurements were taken at baseline, 3-, 6-, 9- and 12-months.

Results: A 35-year old white male presented with unilateral ON in the right eye, and was treated with high dose intravenous methylprednisolone according to the Optic Neuritis Treatment Trial protocol. The patient was asymptomatic for over 4 years, then presented with ON in the left eye and a large hyperintense MRI brain lesion. OCT demonstrated markedly decreased RNFL thickness in the right eye and mild RNFL loss in the left eye. Upon diagnosis with remitting/relapsing MS, the patient was treated with methylprednisolone, followed by Rebif sc 44 mcg tiw. Visual measures improved, and the MRI lesion resolved with a small area of decreased signal intensity. Serial OCT analysis demonstrated continued axonal loss in the right eye but a slow increase in RNFL thickness in a subset of sectors in the left eye. Rebif therapy was well tolerated and the patient has been relapse-free during the last 24 months without evidence of new MRI lesions.

Conclusions: OCT is a reliable and non-invasive means of quantifying axon loss/survival. Our preliminary observations in ON patients suggest that, even in the absence of clinical symptoms, RFNL thickness in the unaffected eye may decrease over time. Evidence from this case study suggests subclinical OCT changes in ON may be halted and potentially reversed with early, aggressive treatment of IFN beta-1a sc.

Early diagnosis and aggressive treatment with IFN beta may improve long-term clinical outcomes.

Example 2

In Vivo Neuroprotection with High Dose, High Frequency Interferon Therapy

A Serial Optical Coherence Tomography Study in Multiple Sclerosis and Optic Neuritis Objective: Optical coherence tomography (OCT) measures retinal nerve fiber layer (RNFL) thickness. This study used serial OCT in patients with remitting/relapsing multiple sclerosis (RRMS) and optic neuritis (ON) to assess axonal changes concurrent with high dose, high frequency interferon beta-1a sc (Rebif) therapy.
Methods: Patients (N=18) in this ongoing prospective open label proof-of-concept study were included if they had RRMS and unilateral ON and were excluded if they had edema of the optic nerve at baseline or were currently treated with other DMTs. Patients were treated with pulse IV methylprednisolone (MP) according to the Optic Neuritis Treatment Trial protocol, followed immediately by Rebif at 22 mcg tiw titrated to 44 mcg tiw within 2 weeks. RNFL thickness was measured at 12 sectors per eye with Stratus OCT at baseline, 3, 6, 9, and 12 months. Paired t-tests compared changes from baseline to each time point for affected and unaffected eyes separately. MRI data were analyzed for correlation with OCT in each eye type. Response (>4% increase from baseline) was analyzed by sector and number of responding sectors in each eye type.
Results: Our preliminary observations in ON patients suggest that, in addition to rapid axonal loss in the affected eye, patients may have subclinical axonal loss in the clinically unaffected eye, even in the absence of clinical symptoms. Although RNFL thickness decreased significantly in 5 sectors by 3 months and 6 sectors by last post-baseline visit (up to 12 months) in clinically affected eyes, clinically unaffected eyes had no significant changes at 3 months or last post-baseline visit.
Conclusions: Our results suggest that treatment with MP and Rebif maintains RNFL thickness in the unaffected eye and may thereby provide a neuroprotective effect. Our data demonstrate the utility of OCT in early diagnosis of ON and MS, permits early and aggressive treatment, which may slowdown, halt and/or potentially reverse subclinical OCT changes in ON and may promote better long-term prognosis.

The invention claimed is:

1. A method for treating a patient having a subclinical decrease in a retinal nerve fiber layer (RNFL) thickness in at least one eye, comprising sequentially or simultaneously administering an immunosuppressive compound and an interferon-beta protein to the patient, wherein the interferon-beta protein is administered at a cumulative weekly dose of more than 12 million international units (MIU), wherein said method treats the subclinical decrease in the RNFL thickness, wherein the patient is not at a high risk of developing clinically definite multiple sclerosis (CDMS) according to magnetic resonance imaging (MRI) criteria, and wherein the interferon-beta protein is a natural IFN-β or IFN-β produced by recombinant means.

2. The method according to claim 1, wherein the cumulative weekly dose is equal or more than 16 MIU, equal or more than 20 MIU, equal or more than 24 MIU, equal or more than 28 MIU, equal or more than 32 MIU, equal or more than 36 MIU, or equal or more than 40 MIU.

3. The method according to claim 1, wherein the patient does not have 3 or more white matter lesions above 3 mm in diameter.

4. The method according to claim 1, wherein the patient does not have a white matter lesion above 3 mm in diameter.

5. The method according to claim 1, wherein the patient does not have a periventricular or an ovoid white matter lesion.

6. The method according to claim 1, wherein the patient clinically manifests optical neuritis (ON) in only one optical nerve.

7. The method according to claim 1, wherein ON is not clinically manifest in the patient.

8. The method according to claim 1, wherein the patient has an isolated clinical symptom of ON.

9. The method according to claim 1, wherein the patient has a decrease in retinal nerve fiber layer (RNFL) thickness of no more than 30 micron in at least one eye at the onset of treatment.

10. The method according to claim 1, wherein the patient has a decrease in retinal nerve fiber layer (RNFL) thickness of at least 10, 7.5 or 5 micron in at least one eye.

11. The method according to claim 1, wherein the interferon-beta is interferon-beta 1a.

12. The method according to claim 1, wherein the interferon-beta is interferon-beta 1b.

13. The method according to claim 1, wherein the interferon-beta protein is administered subcutaneously.

14. The method according to claim 1, wherein the interferon-beta protein is administered intramuscularly.

---

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Linker peptide sequence

<400> SEQUENCE: 1

Glu Phe Gly Ala Gly Leu Val Leu Gly Gly Gln Phe Met
 1               5                  10
```

15. The method according to claim 1, wherein the interferon-beta is a long-acting interferon-beta.

16. The method according to claim 15, wherein the long-acting interferon-beta is selected from pegylated interferon-beta or interferon-beta Fc-fusion proteins.

17. The method according to claim 1, wherein the interferon-beta is dosed at least at 44 mcg s.c, per administration.

18. The method according to claim 1, wherein the interferon-beta is administered at least 3× weekly.

19. The method according to claim 1, wherein the interferon-beta is dosed at 44 mcg s.c. 3× weekly.

20. The method according to claim 1, wherein the interferon-beta is titrated to a dosage of at least 44 mcg s.c. 3× weekly within an interval of no more than 28 days-after termination of treatment with the immunosupressive compound.

21. The method according to claim 1, wherein the immunosuppressive compound is a steroid compound.

22. The method according to claim 21, wherein the steroid compound is selected from the group of methylprednisolone, prednisone or dexamethasone, or steroid-secreting agents.

23. The method according to claim 21, wherein the steroid compound is methylprednisolone.

24. The method according to claim 1, wherein the administration is sequential.

25. The method according to claim 1, wherein the administration of the immunosupressive compound precedes the administration of the interferon-beta protein.

26. The method according to claim 1, wherein the immunosupressive compound is administered in at least two separate dosages.

27. The method according to claim 21, wherein the steroid compound is administered in accordance with the Optic Neuritis Treatment Trial (ONTT) Protocol.

28. The method according to claim 1, wherein a further multiple sclerosis (MS) therapeutic compound is administered to the patient.

29. The method according to claim 28, wherein the further MS therapeutic compound is administered sequentially or simultaneously.

30. The method according to claim 28, wherein the further MS therapeutic compound is selected from the group of sphingosine-1-phosphate (S1 P) receptor agonists, immunosuppressants, adenosine deaminase inhibitors, IV immunoglobulin G, monoclonal antibodies to T-cell surface markers, TH2 promoting cytokines, compounds which inhibit expression of TH1 promoting cytokines, antispasticity agents, AMPA glutamate receptor antagonists, inhibitors of VCAM-1 expression or antagonists of its ligand, anti-macrophage migration inhibitory factor, cathepsin S inhibitors and mTOR inhibitors.

31. The method according to claim 22, wherein the steroid-secreting agent is ACTH.

* * * * *